(12) United States Patent
Beger et al.

(10) Patent No.: US 7,172,600 B2
(45) Date of Patent: Feb. 6, 2007

(54) LOCKING MECHANISM FOR A BONE SCREW

(75) Inventors: Jens Beger, Tuttlingen (DE); Rudolf Zepf, Wurmlingen (DE); Rudolf Beisse, Murnau (DE); Michael Potulski, Murnau (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 10/763,961

(22) Filed: Jan. 23, 2004

(65) Prior Publication Data

US 2004/0153092 A1 Aug. 5, 2004

Related U.S. Application Data

(62) Division of application No. 10/038,376, filed on Jan. 3, 2002, now Pat. No. 6,702,817.

(60) Provisional application No. 60/262,968, filed on Jan. 19, 2001.

(51) Int. Cl.
*A61B 17/58* (2006.01)
*A61F 2/00* (2006.01)

(52) U.S. Cl. ........................... 606/104
(58) Field of Classification Search ............ 128/898; 606/69, 61, 104, 73, 72, 60, 65, 66, 70, 71; 411/352, 353, 970, 999
See application file for complete search history.

(56) References Cited

U.S. PATENT DOCUMENTS 2,248,054 A * 7/1941 Becker ................ 81/457
4,978,349 A * 12/1990 Frigg .................. 606/67
5,275,601 A 1/1994 Gogolewski et al.
5,578,034 A 11/1996 Estes (Continued)

FOREIGN PATENT DOCUMENTS

EP 0 599 640 6/1994

(Continued)

OTHER PUBLICATIONS

*Advertisement for Profile Compression Plate*, Depuy Motech, Inc., 1998 (2 pages).

(Continued)

*Primary Examiner*—Eduardo C Robert
*Assistant Examiner*—Anu Ramana
(74) *Attorney, Agent, or Firm*—Lipsitz & McAllister, LLC

(57) ABSTRACT

A locking mechanism for securing a bone screw 20 to a clamping element 30 of an osteosynthesis holding system 5 is provided. The bone screw 20 has a circumferential groove 25 located on a top portion of the screw 20 below a screw head 22. Snap catches 35 protrude from a bone-contacting surface 38 of the clamping element 30 and interlock with the groove 25 in the screw 20 when the screw 20 is inserted into the clamping element 30 (e.g., when the screw is screwed into a bone segment through a hole in the clamping element). A removal device 90 is provided for removing the screw 20, as a greater axial force is required to overcome the locking mechanism than is needed to engage the locking mechanism. A method for revision (removal) of the screw 20 from the locking mechanism is also provided.

22 Claims, 6 Drawing Sheets

U.S. PATENT DOCUMENTS

| | | | |
|---|---|---|---|
| 5,681,135 A * | 10/1997 | Simonson | 411/5 |
| 5,681,312 A * | 10/1997 | Yuan et al. | 606/61 |
| 5,713,900 A * | 2/1998 | Benzel et al. | 606/61 |
| 5,735,853 A | 4/1998 | Olerud | |
| 5,843,082 A | 12/1998 | Yuan et al. | |
| 5,997,541 A * | 12/1999 | Schenk | 606/73 |
| 6,197,028 B1 | 3/2001 | Ray et al. | |
| 6,206,879 B1 | 3/2001 | Marnay et al. | |
| 6,235,034 B1 * | 5/2001 | Bray | 606/71 |
| 6,241,731 B1 * | 6/2001 | Fiz | 606/65 |
| 6,258,092 B1 * | 7/2001 | Dall | 606/73 |
| 6,331,179 B1 | 12/2001 | Freid et al. | |
| 6,436,100 B1 * | 8/2002 | Berger | 606/73 |
| 6,575,975 B2 * | 6/2003 | Brace et al. | 606/69 |
| 6,599,290 B2 * | 7/2003 | Bailey et al. | 606/69 |
| 6,602,255 B1 * | 8/2003 | Campbell et al. | 606/69 |
| 6,605,090 B1 | 8/2003 | Trieu et al. | |
| 6,702,817 B2 * | 3/2004 | Beger et al. | 606/69 |
| 2002/0058940 A1 | 5/2002 | Frigg et al. | |
| 2002/0099386 A1 * | 7/2002 | Beger et al. | 606/104 |
| 2002/0169453 A1 * | 11/2002 | Berger | 606/73 |
| 2003/0187438 A1 | 10/2003 | Assaker et al. | |

FOREIGN PATENT DOCUMENTS

| | | |
|---|---|---|
| FR | 2 766 353 | 1/1999 |
| WO | 96/08206 | 3/1996 |
| WO | 96/39975 | 12/1996 |
| WO | 97/19646 | 6/1997 |
| WO | 97/20513 | 6/1997 |
| WO | 97/22306 | 6/1997 |
| WO | 98/51226 | 11/1998 |

OTHER PUBLICATIONS

Information regarding the VentroFix implant by Synthes. Although the date of publication of this information is unknown by Applicants, it is Applicants' understanding that the Ventrofix product was available before Applicants' priority date (4 pages).

* cited by examiner

LOCKING MECHANISM FOR A BONE SCREW

This application is a divisional of U.S. patent application Ser. No. 10/038,376 filed on Jan. 3, 2002 which application claims the benefit of U.S. provisional patent application No. 60/262,968 filed on Jan. 19, 2001.

BACKGROUND OF THE INVENTION

The present invention relates generally to osteosynthesis holding systems, such as those used for stabilization of the spinal column. In particular, a locking mechanism for securing a bone screw to a clamping element of an osteosynthesis holding system is provided. A removal device is provided for removing the bone screw, as a greater axial force is required to overcome the locking mechanism than is needed to engage the locking mechanism. A corresponding method for revision (removal) of the bone screw from the locking mechanism is also provided.

It is well known that in osteosynthesis holding systems in general, and in those systems used for stabilization of the spinal column in particular, a loosening of the bone screw which secures the clamping element to the bone segment occurs. When the bone screw becomes loose, the bone screw may move in an axial direction (i.e. a backing out of the screw may occur). This axial movement may result in a loosening of the entire system, as well as injury to the patient by the protruding screw. For example, injury of blood vessels and nerves in the cervical spine and esophagus are common.

Several alternatives exist for securing the bone screw to the bone plate or clamping element. For example, attachment or locking screws or expansion elements may be used to secure the bone screw in place.

It would be advantageous to provide a locking mechanism for a bone screw where no additional securing elements are necessary. It would be further advantageous to provide a locking mechanism where no active locking of the bone screw is needed. It would be still further advantageous if the connection formed by the locking mechanism is reversible, to provide for explantation (removal) of the bone screw. In addition, it would be advantageous if the locking mechanism allows for a pre-stressing of the bone screw between the clamping element and the bone segment after the locking element is engaged.

The methods and apparatus of the present invention provide the foregoing and other advantages.

SUMMARY OF THE INVENTION

The present invention relates to a locking mechanism for securing a bone screw to a clamping element of an osteosynthesis holding system. The bone screw is provided with a circumferential groove located on a top portion of the screw below a screw head. Snap catches are provided on the clamping element. The snap catches protrude from a bone-contacting surface of the clamping element and interlock with the groove in the bone screw when the bone screw is inserted into the clamping element (e.g., when the screw is screwed into a bone segment through a hole in the clamping element). A removal device is provided for removing the bone screw, as a greater axial force is required to overcome the locking mechanism than is needed to engage the locking mechanism. A corresponding method for revision (removal) of the bone screw from the locking mechanism is also provided.

In an exemplary embodiment, a locking mechanism for a bone screw is provided. The locking mechanism includes a clamping element for stabilizing bone segments. The clamping element has at least two snap catches which protrude from a bone-contacting surface of the clamping element and are spaced around an edge of a screw hole. A bone screw is provided which has a circumferential groove located on a top portion thereof below a screw head, for receipt of said snap catches. The snap catches interlock with the groove to secure said bone screw to the clamping element when the bone screw is inserted into the clamping element.

The snap catches may comprise spikes adapted to act as bone anchors. These spikes provide additional anchoring of the clamping element into the bone segment. The spikes may comprise elastic spring elements which snap into the groove when the bone screw is inserted into the clamping element.

In a preferred embodiment, the bone screw is removable from the clamping element after the snap catches interlock with the groove. However, it is preferable if a greater axial force is needed to remove the screw from the clamping element than is needed to insert the screw into the clamping element. Removal of the screw from the clamping element may result in deformation of the snap catches and/or the groove.

The screw may have a shaft having a conical portion between the groove and threads of the shaft. The groove may have a flat edge portion perpendicular to the shaft of the screw. The snap catches may have a square end portion for interlocking with the flat edge portion. Removal of the screw from the clamping element may result in deformation of at least one of (i) the square end portion of the snap catches, or (ii) the flat edge portion of the groove.

A targeting instrument may be placed on the clamping element to provide for correct axial positioning of the screw. The screw is screwed through the clamping element and into the bone segment via the targeting instrument.

The screw may be a cannulated screw. The cannulated screw may be positioned on the bone segment via a Kirschner wire.

The screw may be rotatable after interlocking with the clamping element in order to achieve further pre-stress between the bone segment and the clamping element.

The screw may be a cannulated screw having internal threads in a cannulated portion thereof. The screw may be removable from the clamping element using a removal device having (i) an externally threaded distal end for engagement with the internal threads of the cannulated portion of the screw, and (ii) a handle at a proximal end. The removal device is adapted to be inserted into the screw via a cannulated screwdriver. Removal of the screw is possible by unscrewing the screw from the bone segment using the cannulated screwdriver while simultaneously pulling on the removal device.

The invention further provides for a removal device for revision (removal) of an internally threaded cannulated bone screw. The removal device has a wire body with external threads at a distal end thereof for engagement with the internal threads of the screw. A handle is provided at a proximal end of the wire body for use in pulling the removal device after engagement with the cannulated screw.

The removal device is adapted for insertion into a cannulated instrument, such as a cannulated screwdriver.

The invention also provides a method for revision of an implanted cannulated bone screw. A cannulated screwdriver is inserted into a screw head of the cannulated bone screw. A removal device is inserted into the cannulated screwdriver. An externally threaded distal end of the removal device is screwed into an internally threaded portion of the cannulated screw. Once the removal device is screwed into the cannulated bone screw, the screw can be removed (e.g., from a bone segment) by simultaneously unscrewing the screw using the cannulated screwdriver and pulling the screw using a handle located on a proximal end of the removal device.

The bone screw to be removed may secure a clamping element to a bone segment. A locking mechanism may secure the bone screw to the clamping element. The locking mechanism comprises at least two snap catches protruding from a bone-contacting surface of the clamping element and spaced around an edge of a screw hole. A circumferential groove is located on a top portion of the screw below a screw head for receipt of the snap catches. The snap catches interlock with the groove to secure the bone screw to the clamping element when the bone screw is screwed into the bone segment through the screw hole of the clamping element.

The snap catches may comprise spikes adapted to function as bone anchors. The spikes may comprise elastic spring elements which snap into the groove when the bone screw is inserted into the clamping element. A greater axial force may be needed to remove the screw from the clamping element than is needed to insert the screw into the clamping element. Removal of the screw from the clamping element results in deformation of at least one of (i) the snap catches, or (ii) the groove.

The screw comprises a shaft having a conical portion between the groove and threads of the shaft. The groove may have a flat edge portion perpendicular to a shaft of the screw. The snap catches may have a square end portion for interlocking with the flat edge portion. Removal of the screw from the clamping element results in deformation of at least one of (i) the square end portion of the snap catches, or (ii) the flat edge portion of the groove.

The screw may be rotatable after interlocking with the clamping element in order to achieve further pre-stress between the bone segment and the clamping element.

A method for locking a bone screw to a clamping element is also provided. A clamping element for stabilizing bone segments is provided. The clamping element has at least two snap catches protruding from a bone-contacting surface of the clamping element and spaced around an edge of a screw hole. A bone screw is provided which has a circumferential groove located on a top portion thereof below a screw head, for receipt of said snap catches. The bone screw is screwed into the bone segment through the screw hole of the clamping element until the snap catches interlock with the groove to secure the bone screw to the clamping element.

The snap catches may comprise spikes adapted to function as bone anchors. The spikes may comprise elastic spring elements which snap into the groove when the bone screw is inserted into the clamping element.

The bone screw may be removable from the clamping element after the snap catches interlock with the groove. A greater axial force may be needed to remove the screw from the clamping element than is needed to insert the screw into the clamping element. Removal of the screw from the clamping element may result in deformation of at least one of (i) the snap catches, or (ii) the groove.

The screw may comprise a shaft having a conical portion between the groove and threads of the shaft. The groove may have a flat edge portion perpendicular to a shaft of the screw. The snap catches may have a square end portion for interlocking with the flat edge portion. Removal of the screw from the clamping element may result in deformation of at least one of (i) the square end portion of the snap catches, or (ii) the flat edge portion of the groove.

A targeting instrument may be placed on the clamping element to provide for correct axial positioning of the screw. The screw may be screwed through the clamping element and into the bone segment via the targeting instrument.

The screw may be a cannulated screw. The cannulated screw may be positioned on the bone segment via a Kirschner wire.

The screw may be rotatable after interlocking with the clamping element in order to achieve further pre-stress between the bone segment and the clamping element.

The screw may be a cannulated screw having internal threads in a cannulated portion thereof.

BRIEF DESCRIPTION OF THE DRAWINGS

The present invention will hereinafter be described in conjunction with the appended drawing figures, wherein like numerals denote like elements, and.

DETAILED DESCRIPTION OF THE INVENTION

The ensuing detailed description provides preferred exemplary embodiments only, and is not intended to limit the scope, applicability, or configuration of the invention. Rather, the detailed description of the preferred exemplary embodiments will provide those skilled in the art with an enabling description for implementing a preferred embodiment of the invention. It should be understood that various changes may be made in the function and arrangement of elements without departing from the spirit and scope of the invention as set forth in the appended claims.

The present invention relates to a locking mechanism for securing a bone screw to a clamping element of an osteosynthesis holding system. An example embodiment of an osteosynthesis holding system with which the present invention can be implemented is described in detail in commonly assigned U.S. Pat. No. 6,206,879 entitled "Osteosynthetic Holding System." Although the present invention will be described in connection with a twin screw osteosynthesis holding system of the type described in U.S. Pat. No. 6,206,879, those skilled in the art will appreciate that the locking mechanism of the present invention can be utilized in a single screw osteosynthesis holding systems, as well as a wide variety of applications where a screw needs to be secured to a clamping element or similar device.

Figure 1:
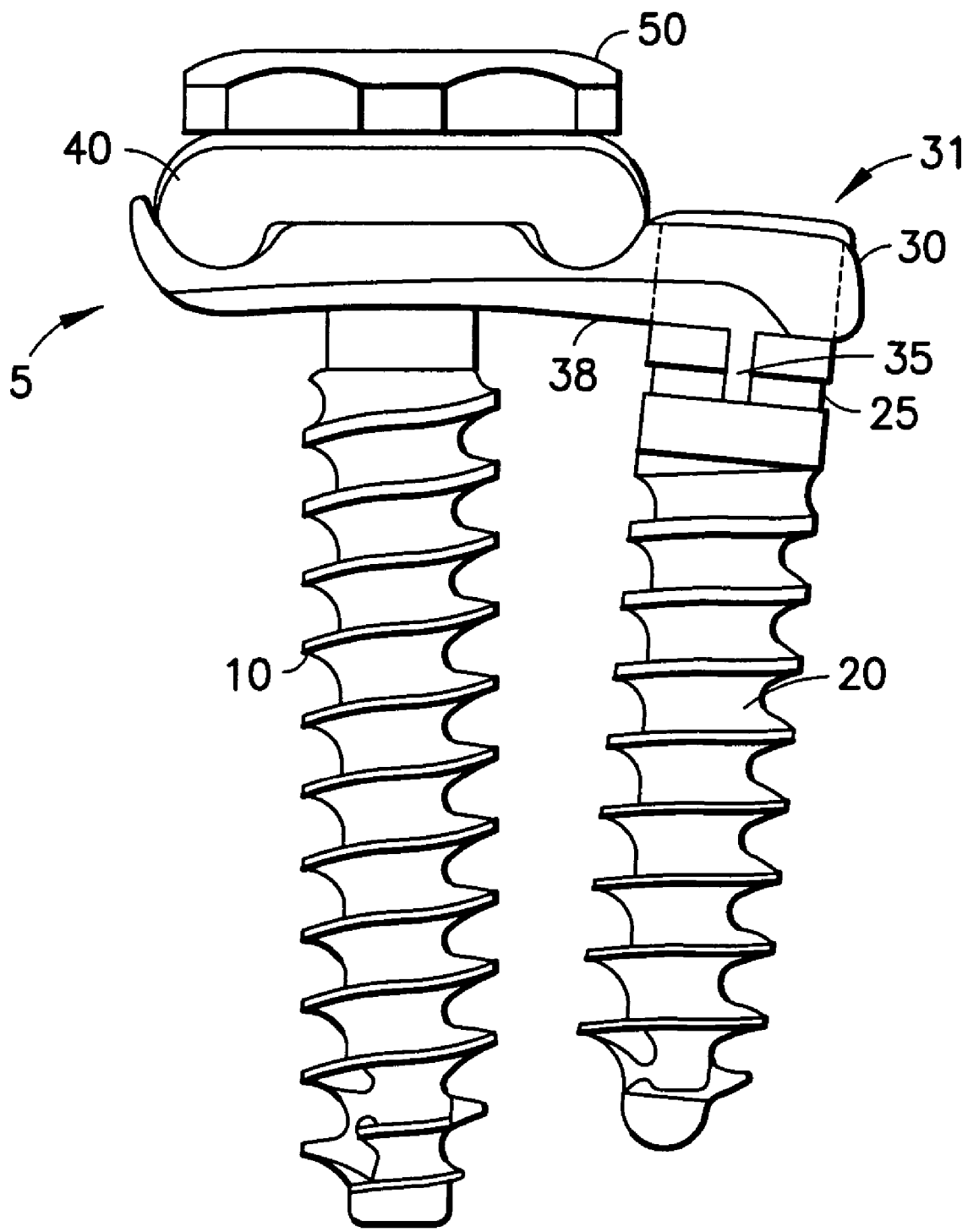
FIG. 1 shows an example of an osteosynthesis holding system with one embodiment of the locking mechanism of the present invention.

FIG. 1 shows an end view of an exemplary embodiment of an osteosynthesis holding system 5 with the locking mechanism of the present invention. A brief description of the osteosynthesis holding system will enable better understanding of the inventive locking mechanism. The osteosynthesis holding system 5 is a twin screw holding system, having a stabilizing screw 10 and an anchoring screw 20. A clamping element 30 is provided which secures a connector 40 (which can comprise, e.g., a plate or rods or the like) in position on a bone segment (not shown) by tightening a fixation nut 50, which screws onto stabilizing screw 10. The connector 40 is clamped at each end by respective clamping elements 30 which are anchored to respective bone segments for stabilizing the bone segments relative to one another.

Figure 2:
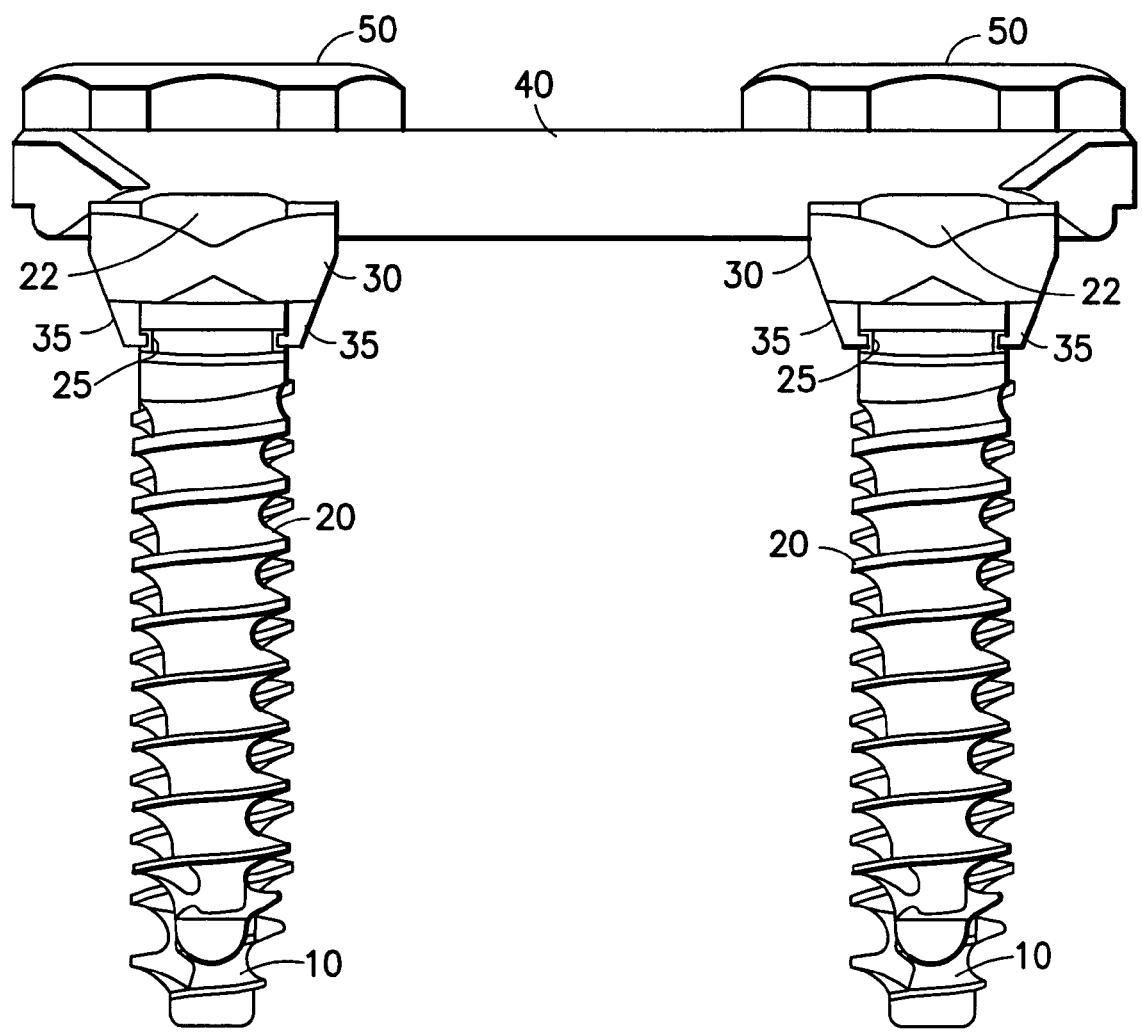
FIG. 2 shows a side view of the osteosynthesis holding system of FIG. 1.

A side view of the osteosynthesis holding system 5 of FIG. 1 is shown in FIG. 2. FIG. 2 shows the osteosynthesis holding system assembled to connect two bone segments (not shown). Therefore, a clamping element 30 is provided for each bone segment, and a corresponding anchor screw 20 is also provided for each segment. The connector 40 spans the two clamping elements and is secured to each by a respective fixation nut 50. Respective stabilizing screws 10 are also provided for each clamping element 30.

Figure 3:
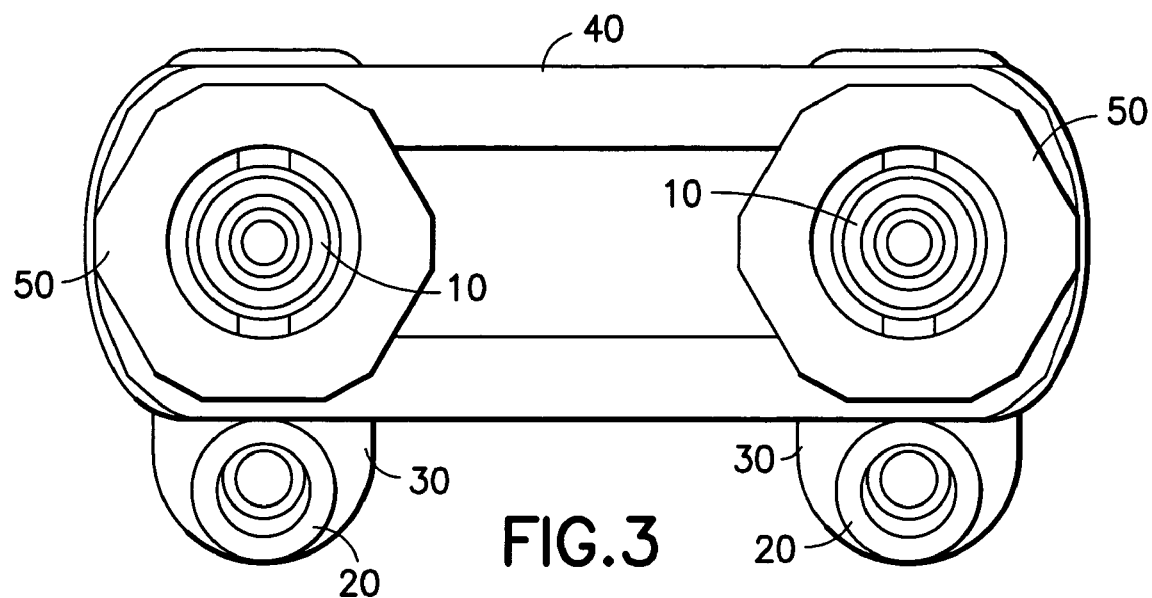
FIG. 3 shows a top view of the osteosynthesis holding system of FIG. 2.

FIG. 3 shows a top view of the osteosynthesis holding system 5 of FIGS. 1 and 2. The top view of FIG. 3 shows the connector 40 spanning the two clamping elements 30, and secured thereto by respective fixation nuts 50 on respective stabilizing screws 10. Respective anchoring screws 20 are also provided for each clamping element 30.

In the example embodiment of the invention shown in FIGS. 1–3, a locking mechanism for a bone screw (e.g., anchoring screw 20) is provided. The locking mechanism includes a clamping element 30 for stabilizing bone segments. The clamping element 30 has at least two snap catches 35 which protrude from a bone-contacting surface 38 of the clamping element 30 and are spaced around an edge of a screw hole 31 (shown in dot-dashed lines) in the clamping element 30. A bone screw 20 is provided which has a circumferential groove 25 located on a top portion thereof below a screw head 22, for receipt of said snap catches. The snap catches 35 interlock with the groove 25 to secure the bone screw 20 to the clamping element 30 when the bone screw 20 is inserted into the clamping element 30.

No positive locking is required with the locking mechanism of the present invention, as the snap catches 35 automatically lock into the groove 25 when the bone screw 20 is inserted into the clamping element 30 and tightened so as to secure the clamping element 30 to the bone segment.

Figure 4:
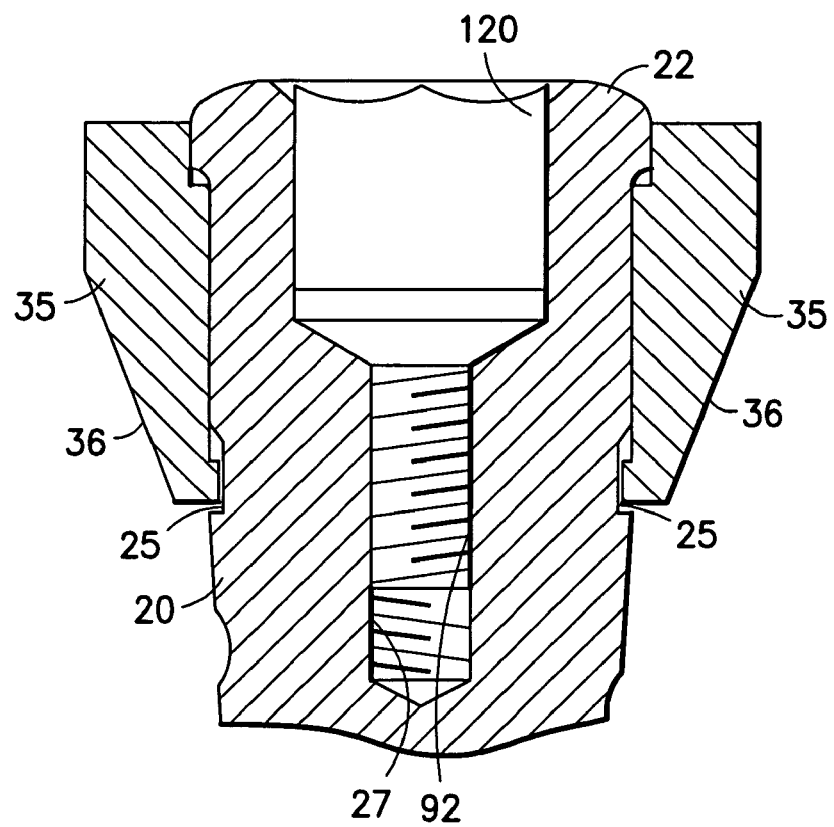
FIG. 4 shows an example embodiment of the locking mechanism of the present invention.

FIG. 4 shows an example embodiment of the locking mechanism of the present invention. Snap catches 35 protrude from a bone contacting surface of the clamping element 30 (only partially shown in FIG. 4). The snap catches 35 may comprise spikes 36 adapted to act as bone anchors. These spikes 36 provide additional anchoring of the clamping element 30 into the bone segment.

The spikes 36 may comprise elastic spring elements which snap into the groove 25 when the bone screw 20 is inserted into the clamping element 30. For example, the spikes 36 may have a resilient structure that enables the snap catches 35 to be expanded by the insertion of the screw 20 into the clamping element 30. When the screw 20 is sufficiently inserted into the clamping element 30 such that the groove 25 aligns with the snap catches 35, the snap catches resiliently return to their natural position, thereby interlocking with the groove 25.

As shown in FIG. 4, the screw 20 may be a cannulated screw having internal threads 27 in a cannulated portion thereof.

In a preferred embodiment, the bone screw 20 is removable from the clamping element 30 after the snap catches 35 interlock with the groove 25. However, it is preferable if a greater axial force is needed to remove the screw 20 from the clamping element 30 than is needed to insert the screw 20 into the clamping element 30. Removal of the screw 20 from the clamping element 30 may result in deformation of the snap catches 35 and/or the groove 25.

Figure 5:
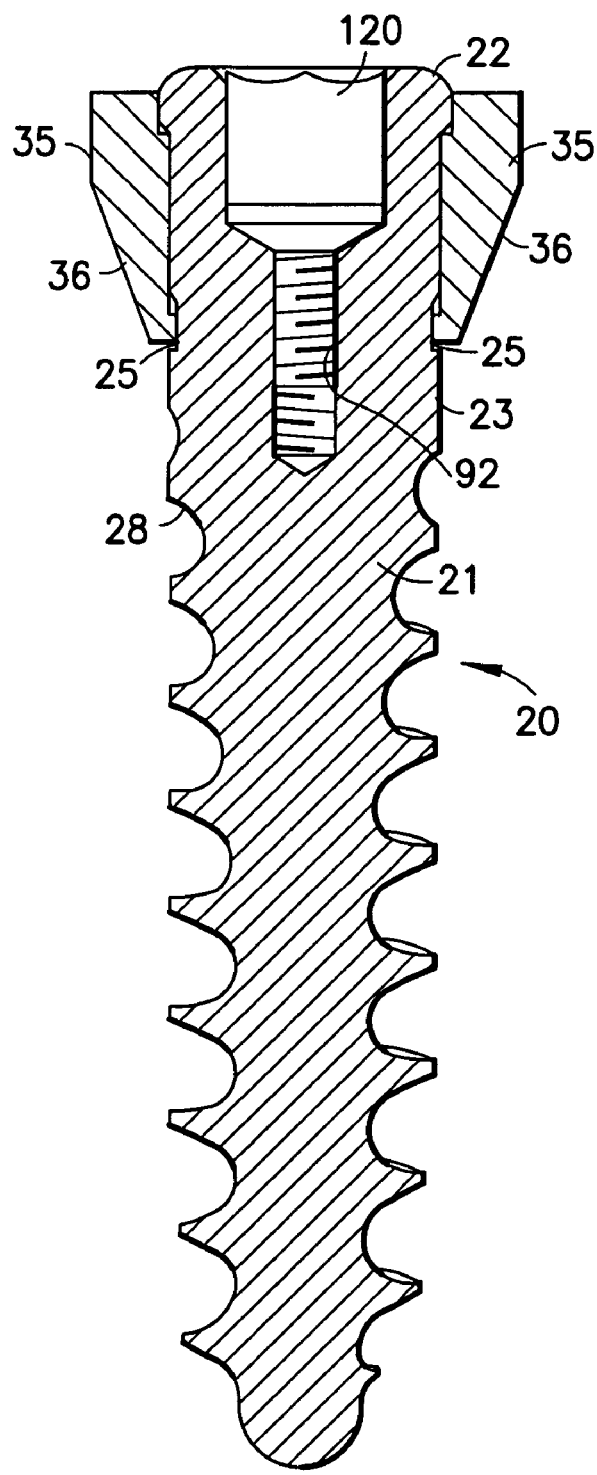
FIG. 5 shows an example embodiment of the locking mechanism of the present invention.
Figure 6:
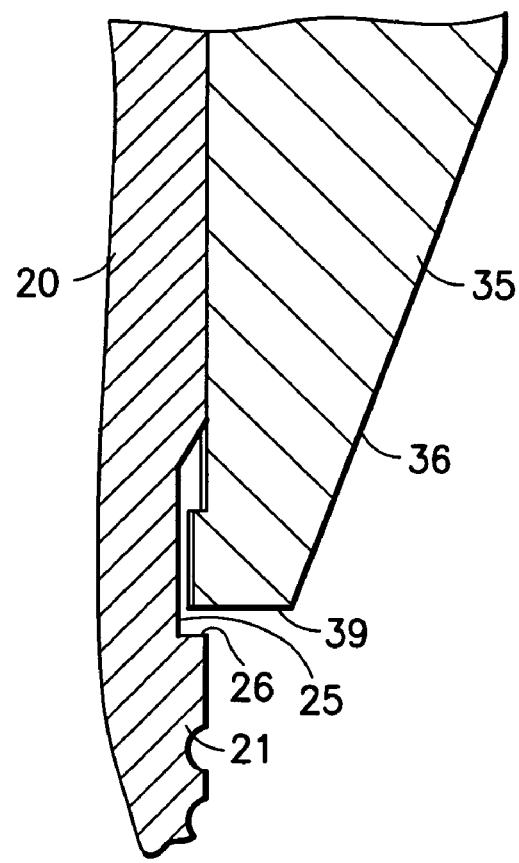
FIG. 6 shows a close up view of an example embodiment of the present invention.

As shown in FIG. 5, the screw 20 may have a shaft 21 having a conical portion 23 between the groove 25 and threads 28 of the shaft 21. As shown in FIG. 6, the groove 25 may have a flat edge portion 26 perpendicular to the shaft 21 of the screw 20. The snap catches 35 may have a square end portion 39 for interlocking with the flat edge portion 26 of the groove 25. Removal of the screw 20 from the clamping element 30 may result in deformation of at least one of (i) the square end portion 39 of the snap catches 35, or (ii) the flat edge portion 26 of the groove 25.

Figure 7:
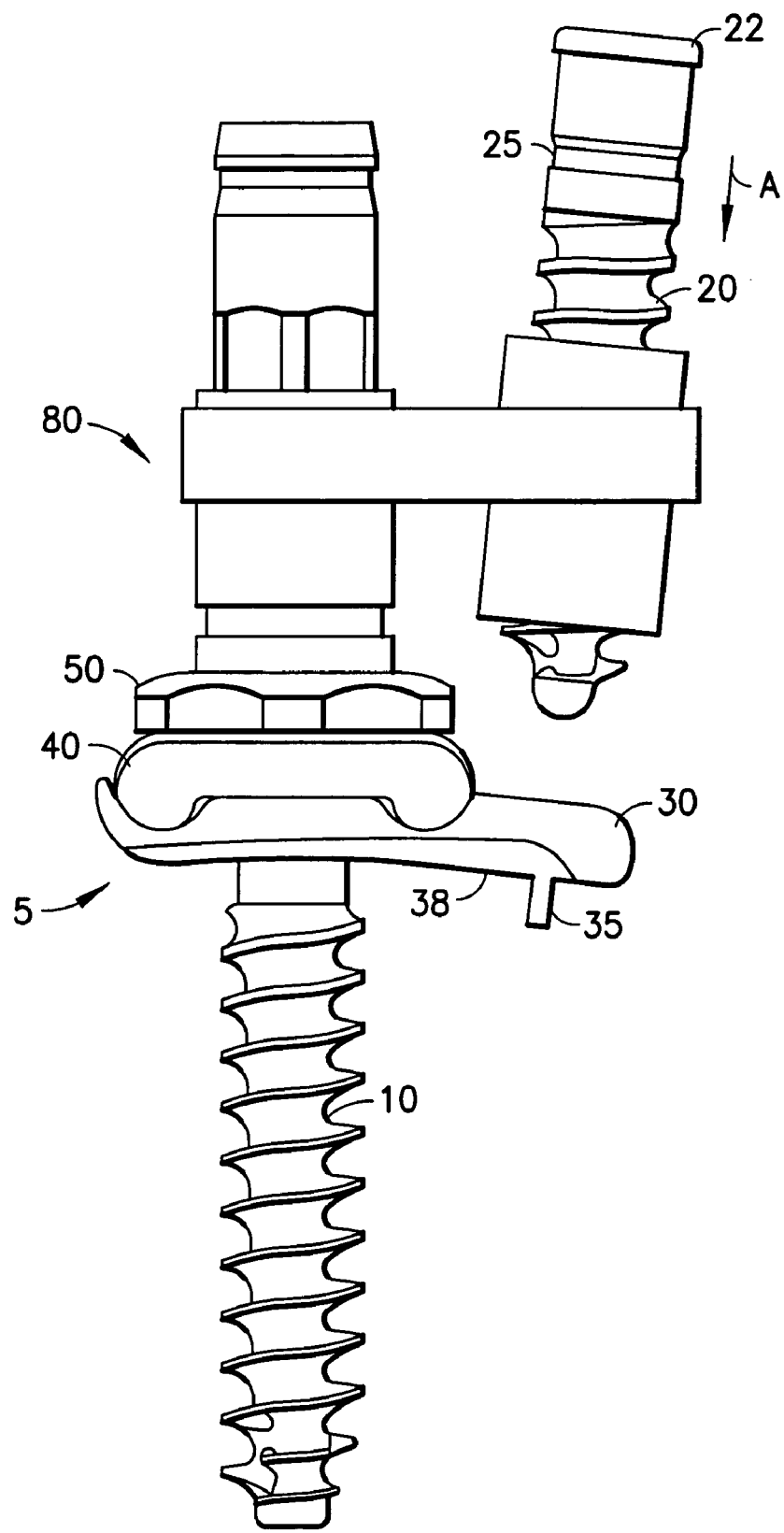
FIG. 7 shows a targeting instrument for use in inserting a bone screw into an osteosynthesis plating system which utilizes an embodiment of the locking mechanism of the present invention.

As shown in FIG. 7, a targeting instrument 80 may be placed on the clamping element 30 to provide for correct axial positioning of the screw 20. The screw 20 is inserted through the targeting instrument 80 in the direction indicated by arrow A and into a screw hole of the clamping element 30. The screw 20 is then screwed through the clamping element 30 and into the bone segment (not shown) via the targeting instrument.

The screw 20 may be a cannulated screw. The cannulated screw may be positioned on the bone segment via a Kirschner wire as well known in the art.

The screw 20 may be rotatable after interlocking with the clamping element 30 in order to achieve further pre-stress between the bone segment and the clamping element 30.

Figure 8:
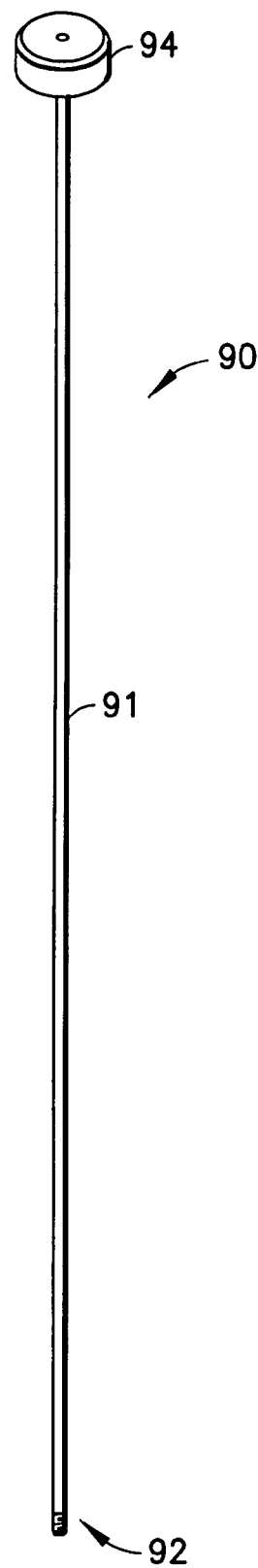
FIG. 8 shows a removal device for use in removing a screw from an osteosynthesis plating system having a locking mechanism in accordance with the present invention.

As shown in FIG. 8, the invention further provides for a removal device 90 for revision (removal) of an internally threaded cannulated bone screw 20. The removal device 90 has a wire body 91 with external threads 92 at a distal end thereof for engagement with the internal threads 27 of screw 20. A handle 94 is provided at a proximal end of the wire body 91 for use in pulling the removal device 90 after engagement with the cannulated screw 20.

Figure 9:
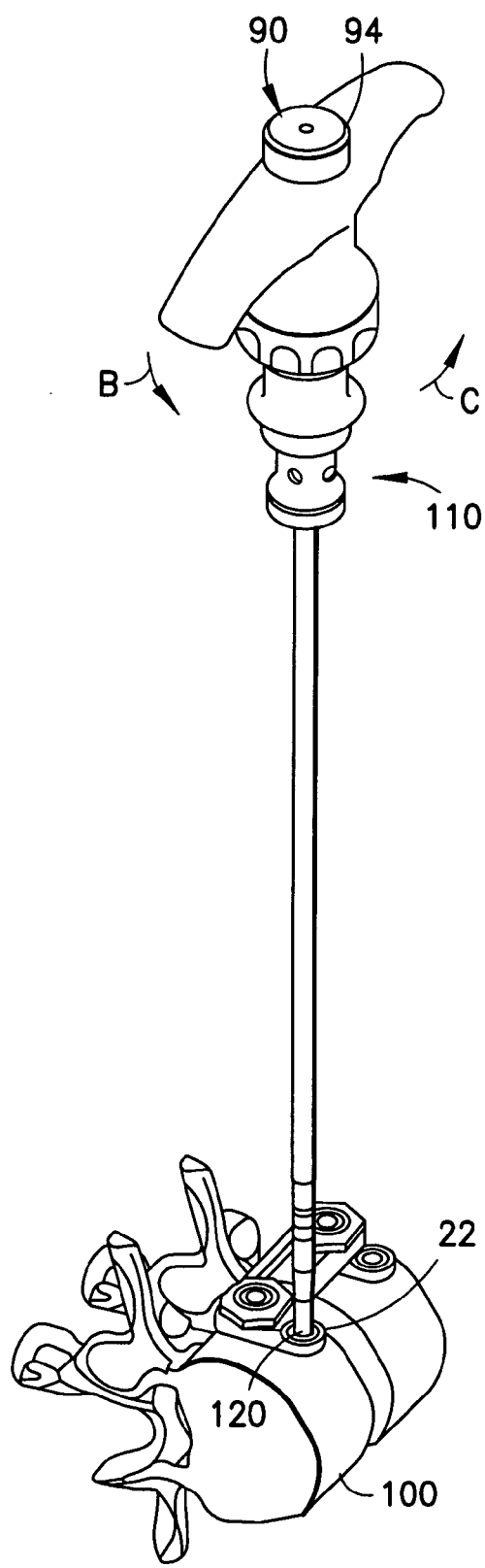
FIG. 9 shows a removal device used with a cannulated screwdriver to remove a screw from an osteosynthesis plating system having a locking mechanism in accordance with the present invention.

As shown in FIG. 9, the removal device 90 is adapted to be inserted into the screw 20 via a cannulated screwdriver 110. Removal of the screw is accomplished by inserting the cannulated screwdriver 110 into a screw head 22 of the cannulated bone screw 20. The cannulated screwdriver has a drive head 120 for engagement with a corresponding recess on the screw head 22. The drive head 120 and corresponding recess in the screw head 22 may be, for example, hexagonal in shape. The removal device 90 is inserted into the cannulated screwdriver 110. As can be seen in FIGS. 4 and 5, an externally threaded distal end 92 of the removal device 90 is screwed into internal threads 27 of the cannulated screw 20. Once the removal device 90 is screwed into the cannulated bone screw 20, the screw 20 can be removed (e.g., from a bone segment 100) by simultaneously unscrewing (Arrow B) the screw using the cannulated screwdriver 110 and pulling (Arrow C) the screw 20 using the handle 94 located on a proximal end of the removal device 90.

Due to the configuration of the locking mechanism of the present invention, a greater axial force may be needed to remove the screw 20 from the clamping element 30 than is needed to insert the screw 20 into the clamping element 30. The removal device 90 provides assistance in generating the axial force required to overcome the locking mechanism. As discussed above, removal of the screw 20 from the clamping element 30 may result in deformation of at least one of (i) the snap catches 35, or (ii) the groove 25.

Corresponding methods for locking the 20 bone screw to the clamping element 30 are also provided. The bone screw 20 is screwed into a bone segment through the screw hole of the clamping element 30 until the snap catches 35 interlock with the groove 25 to secure the bone screw 20 to the clamping element 30. A targeting instrument 80 (FIG. 7) may be placed on the clamping element 30 to provide for correct axial positioning of the screw 20. The screw 20 may be screwed through the clamping element 30 and into the bone segment via the targeting instrument 80.

As noted above, the screw 20 may be a cannulated screw. Moreover, the cannulated screw may be positioned on the bone segment via a Kirschner wire.

It should now be appreciated that the present invention provides advantageous methods and apparatus for locking a bone screw to a clamping element, as well as advantageous methods and apparatus for removing a bone screw with such a locking mechanism from a clamping element.

Although the invention has been described in connection with various illustrated embodiments, numerous modifications and adaptations may be made thereto without departing from the spirit and scope of the invention as set forth in the claims.

What is claimed is:

1. A method for revision of an implanted cannulated bone screw, comprising the steps of:
   inserting a cannulated screwdriver into a screw head of said cannulated bone screw;
   introducing a removal device into said cannulated screwdriver;
   screwing a threaded distal end of said removal device into a corresponding threaded portion of said cannulated screw; and
   simultaneously unscrewing said screw using said cannulated screwdriver and pulling said screw using a handle located on a proximal end of said removal device;
   wherein:
      said bone screw secures a clamping element to a bone segment;
      a locking mechanism secures said bone screw to said clamping element, said locking mechanism comprising:
         at least two snap catches protruding from a bone-contacting surface of said clamping element and spaced around an edge of a screw hole; and
         a circumferential groove located on a top portion of said screw below a screw head for receipt of said snap catches; and
         said snap catches interlock with said groove to secure said bone screw to said clamping element when said bone screw is screwed into said bone segment through said screw hole of said clamping element.

2. A method in accordance with claim 1, wherein the distal end of said removal device is externally threaded and the corresponding threaded portion of said screw is an internally threaded portion.

3. A method in accordance with claim 1, wherein: said snap catches comprise spikes adapted to function as bone anchors.

4. A method in accordance with claim 3, wherein:
   said spikes comprise elastic spring elements; and
   said elastic spring elements snap into said groove when said bone screw is inserted into said clamping element.

5. A method in accordance with claim 1, wherein a greater axial force is needed to remove said screw from said clamping element than is needed to insert said screw into said clamping element.

6. A method in accordance with claim 1, wherein:
   removal of said screw from said clamping element results in deformation of at least one of (i) said snap catches, or (ii) said groove.

7. A method in accordance with claim 1, wherein:
   said screw comprises a shaft having a conical portion between said groove and threads of said shaft.

8. A method in accordance with claim 1, wherein:
   said groove has a flat edge portion perpendicular to a shaft of said screw; and
   said snap catches have a square end portion for interlocking with said flat edge portion.

9. A method in accordance with claim 8, wherein:
   removal of said screw from said clamping element results in deformation of at least one of (i) said square end portion of said snap catches, or (ii) said flat edge portion of said groove.

10. A method in accordance with claim 1, wherein:
    said screw is rotatable after interlocking with said clamping element in order to achieve further pre-stress between said bone segment and said clamping element.

11. A method for locking a bone screw to a clamping element, comprising the steps of:
    providing a clamping element for stabilizing bone segments, having at least two snap catches protruding from a bone-contacting surface of said clamping element and spaced around an edge of a screw hole;
    providing a cannulated bone screw having a circumferential groove located on a top portion thereof below a screw head, for receipt of said snap catches;
    positioning said clamping element on a bone segment to be stabilized;
    positioning said screw on the bone segment via a Kirschner wire; and
    screwing said bone screw into said bone segment through said screw hole of said positioned clamping element in an axial direction until the snap catches interlock with the groove of said bone screw to secure said bone screw to said clamping element.

12. A method in accordance with claim 11, wherein said bone screw is removable from said clamping element after said snap catches interlock with said groove.

13. A method in accordance with claim 12, wherein a greater axial force is needed to remove said screw from said clamping element than is needed to insert said screw into said clamping element.

14. A method in accordance with claim 12, wherein:
    removal of said screw from said clamping element results in deformation of at least one of (i) said snap catches, or (ii) said groove.

15. A method in accordance with claim 11, wherein:
    said screw comprises a shaft having a conical portion between said groove and threads of said shaft.

16. A method in accordance with claim 11, wherein:
    said groove has a flat edge portion perpendicular to a shaft of said screw; and said snap catches have a square end portion for interlocking with said flat edge portion.

17. A method in accordance with claim 16, wherein:
removal of said screw from said clamping element results in deformation of at least one of (i) said square end portion of said snap catches, or (ii) said flat edge portion of said groove.

18. A method in accordance with claim 11, wherein:
a targeting instrument is placed on said clamping element; and
said screw is screwed through said clamping element and into said bone segment via said targeting instrument.

19. A method in accordance with claim 11, wherein:
said screw is rotatable after interlocking with said clamping element in order to achieve further pre-stress between said bone segment and said clamping element.

20. A method in accordance with claim 11, wherein:
said a cannulated screw has internal threads in a cannulated portion thereof.

21. A method for locking a bone screw to a clamping element, comprising the steps of:

providing a clamping element for stabilizing bone segments, having at least two snap catches protruding from a bone-contacting surface of said clamping element and spaced around an edge of a screw hole;

providing a bone screw having a circumferential groove located on a top portion thereof below a screw head, for receipt of said snap catches; and screwing said bone screw into said bone segment through said screw hole of said clamping element until the snap catches interlock with the groove to secure said bone screw to said clamping element;

wherein said snap catches comprise spikes adapted to function as bone anchors.

22. A method in accordance with claim 21, wherein:
said spikes comprise elastic spring elements; and
said elastic spring elements snap into said groove when said bone screw is inserted into said clamping element.

* * * * *